(12) United States Patent
Daroszewski et al.

(10) Patent No.: US 10,456,369 B2
(45) Date of Patent: Oct. 29, 2019

(54) METHODS AND COMPOSITIONS FOR IMPROVING THE HEALTH OF ANIMALS

(75) Inventors: Janusz Daroszewski, Ottawa (CA); Clayton Paul Dick, Guelph (CA); Isabella Verzberger-Epshtein, Stratford (CA)

(73) Assignee: Avivagen Inc., Ottawa (CA)

(*) Notice: Subject to any disclaimer, the term of this patent is extended or adjusted under 35 U.S.C. 154(b) by 717 days.

(21) Appl. No.: 13/318,236

(22) PCT Filed: Apr. 30, 2010

(86) PCT No.: PCT/CA2010/000671
§ 371 (c)(1),
(2), (4) Date: Nov. 6, 2012

(87) PCT Pub. No.: WO2010/124391
PCT Pub. Date: Nov. 4, 2010

(65) Prior Publication Data
US 2013/0131183 A1    May 23, 2013

Related U.S. Application Data

(60) Provisional application No. 61/174,259, filed on Apr. 30, 2009.

(51) Int. Cl.
*A61K 31/12* (2006.01)
*A61K 31/125* (2006.01)
(Continued)

(52) U.S. Cl.
CPC ............ *A61K 31/12* (2013.01); *A23K 20/179* (2016.05); *A23K 50/40* (2016.05); *A61K 9/0056* (2013.01); *A61K 31/336* (2013.01)

(58) Field of Classification Search
CPC .................... A61K 31/12; A61K 9/0056
(Continued)

(56) References Cited

U.S. PATENT DOCUMENTS 2,988,045 A    6/1961    Fisher
3,206,316 A    9/1965    Klaui
(Continued)

FOREIGN PATENT DOCUMENTS

CA    2085212 A1    6/1993
CA    2171625 A1    2/1996
(Continued)

OTHER PUBLICATIONS

Oro, A. E. and Scott, M. P. "Splitting hairs: Dissecting Roles of Signaling Systems in Epidermal Development" in Cell, vol. 95, 575-578, Nov. 25, 1998.*

(Continued)

*Primary Examiner* — Shengjun Wang
(74) *Attorney, Agent, or Firm* — Clark & Elbing LLP

(57) ABSTRACT

The invention features compositions and methods for the administration of an oxidatively transformed carotenoid, or a component thereof, for improving the health of animals, such as increasing joint mobility, increasing activity, and improving coat quality. In particular, methods for improving the health of animals comprise administering compositions comprising an oligomeric material formed by reaction of oxygen with a carotenoid.

30 Claims, 6 Drawing Sheets

(51) Int. Cl.

| | | |
|---|---|---|
| *A61K 47/00* | (2006.01) | |
| *A61K 31/74* | (2006.01) | |
| *A61K 9/00* | (2006.01) | |
| *A61K 31/336* | (2006.01) | |
| *A23K 20/179* | (2016.01) | |
| *A23K 50/40* | (2016.01) | |

(58) Field of Classification Search
USPC .................. 514/690, 691; 424/439, 78.08
See application file for complete search history.

(56) References Cited

U.S. PATENT DOCUMENTS

| | | | |
|---|---|---|---|
| 4,105,855 A | 8/1978 | Schulz et al. | |
| 4,127,455 A | 11/1978 | Schulz et al. | |
| 4,234,575 A | 11/1980 | Weir et al. | |
| 4,333,922 A | 6/1982 | Herschler | |
| 4,351,346 A | 9/1982 | Brummer et al. | |
| 4,642,318 A | 2/1987 | Wolff | |
| 4,702,929 A | 10/1987 | Lehn et al. | |
| 4,889,847 A | 12/1989 | Kligman et al. | |
| 4,996,069 A | 2/1991 | de Hey et al. | |
| 5,047,231 A | 9/1991 | Spanier et al. | |
| 5,084,292 A | 1/1992 | Van Dort et al. | |
| 5,097,063 A | 3/1992 | Moldt | |
| 5,225,604 A | 7/1993 | Moldt | |
| 5,252,604 A | 10/1993 | Nagy et al. | |
| 5,290,605 A | 3/1994 | Shapira | |
| 5,310,554 A | 5/1994 | Haigh | |
| 5,358,915 A | 10/1994 | Nebergall et al. | |
| 5,475,006 A * | 12/1995 | Burton ............... | C07K 5/06139 514/310 |
| 5,527,533 A * | 6/1996 | Tso et al. ................ | 424/422 |
| 5,635,237 A | 6/1997 | Greenberg et al. | |
| 5,646,186 A | 7/1997 | Wang et al. | |
| 5,665,776 A | 9/1997 | Yu et al. | |
| 5,670,548 A | 9/1997 | Bernhard et al. | |
| 5,673,653 A | 10/1997 | Sherrill | |
| 5,719,195 A | 2/1998 | Braiman | |
| 5,744,502 A | 4/1998 | Lignell et al. | |
| 5,759,528 A | 6/1998 | Yamada et al. | |
| 5,874,093 A | 2/1999 | Eliaz et al. | |
| 5,941,197 A | 8/1999 | Axelrod | |
| 5,965,616 A | 10/1999 | Wang et al. | |
| 5,998,395 A | 12/1999 | Kligman | |
| 6,008,254 A | 12/1999 | Kligman et al. | |
| 6,080,393 A | 6/2000 | Liu et al. | |
| 6,083,520 A | 7/2000 | Toneby | |
| 6,093,427 A | 7/2000 | Axelrod | |
| 6,110,521 A | 8/2000 | Axelrod | |
| 6,159,516 A | 12/2000 | Axelrod et al. | |
| 6,207,142 B1 | 3/2001 | Odds et al. | |
| 6,223,693 B1 | 5/2001 | Perlberg et al. | |
| 6,228,887 B1 | 5/2001 | Kligman et al. | |
| 6,251,953 B1 | 6/2001 | Baranowitz | |
| 6,277,420 B1 | 8/2001 | Andersen et al. | |
| 6,296,877 B1 | 10/2001 | Auweter et al. | |
| 6,423,743 B1 | 7/2002 | Romancyzk, Jr. | |
| 6,433,025 B1 | 8/2002 | Lorenz | |
| 6,544,532 B1 | 4/2003 | Jager-Lezer et al. | |
| 6,812,009 B2 | 11/2004 | Gladue et al. | |
| 6,821,538 B2 | 11/2004 | Axelrod et al. | |
| 6,840,196 B2 | 1/2005 | Kirch | |
| 6,886,496 B1 | 5/2005 | Brown | |
| 6,886,497 B1 | 5/2005 | Hague | |
| 6,895,900 B2 | 5/2005 | Hingst | |
| 7,001,889 B2 | 2/2006 | Freehauf et al. | |
| 7,132,458 B2 | 11/2006 | Burton et al. | |
| 8,211,461 B2 | 7/2012 | Burton et al. | |
| 2002/0088403 A1 | 7/2002 | Heinzl et al. | |
| 2002/0165285 A1 | 11/2002 | Runge et al. | |
| 2003/0096875 A1 | 5/2003 | Burton et al. | |
| 2003/0157159 A1 | 8/2003 | Franklin et al. | |
| 2003/0180349 A1 | 9/2003 | Franklin | |
| 2003/0190343 A1 | 10/2003 | Thombre et al. | |
| 2004/0047896 A1 * | 3/2004 | Malnoe et al. ................ | 424/439 |
| 2005/0205086 A1 | 9/2005 | Tamarkin et al. | |
| 2005/0249787 A1 | 11/2005 | Reynolds et al. | |
| 2006/0063835 A1 | 3/2006 | De Paoli Ambrosi et al. | |
| 2006/0127505 A1 * | 6/2006 | Haines et al. ................ | 424/729 |
| 2007/0043046 A1 | 2/2007 | Bernardon et al. | |
| 2007/0098820 A1 * | 5/2007 | Bortlik et al. ................ | 424/725 |
| 2007/0269526 A1 | 11/2007 | Bos et al. | |
| 2007/0282010 A1 | 12/2007 | Aberg | |
| 2007/0298077 A1 | 12/2007 | Jones | |
| 2008/0025929 A1 | 1/2008 | Burton et al. | |
| 2008/0107652 A1 | 5/2008 | Durvasula et al. | |
| 2008/0107768 A1 | 5/2008 | Hinojosa et al. | |
| 2008/0214518 A1 | 9/2008 | Remmal | |
| 2008/0311175 A1 | 12/2008 | Burton et al. | |
| 2009/0306222 A1 | 12/2009 | Burton et al. | |
| 2011/0217244 A1 | 9/2011 | Johnston et al. | |
| 2013/0156816 A1 | 6/2013 | Stobbs et al. | |
| 2016/0287528 A1 | 10/2016 | Stobbs et al. | |

FOREIGN PATENT DOCUMENTS

| | | |
|---|---|---|
| CA | 2221122 A1 | 5/1998 |
| CA | 2357275 A1 | 10/2002 |
| CA | 2455747 A1 | 2/2003 |
| CA | 2474208 A1 | 8/2003 |
| CA | 2495355 A1 | 2/2004 |
| CA | 2648282 A1 | 10/2007 |
| CA | 2171625 C | 10/2008 |
| CA | 2771204 A1 | 11/2010 |
| CA | 2840376 A1 | 12/2012 |
| CN | 1131939 A | 9/1996 |
| CN | 1253498 A | 5/2000 |
| CN | 1505602 A | 6/2004 |
| EP | 0385335 A2 | 9/1990 |
| EP | 0399619 A1 | 11/1990 |
| EP | 0415464 A2 | 3/1991 |
| EP | 0546870 A1 | 6/1993 |
| EP | 0630578 A2 | 12/1994 |
| EP | 0718284 A2 | 6/1996 |
| EP | 1186245 A2 | 3/2002 |
| EP | 1253131 A1 | 10/2002 |
| GB | 1021537 A | 3/1966 |
| GB | 1323800 A | 7/1973 |
| GB | 1502895 A | 3/1978 |
| JP | 06-276956 A | 4/1994 |
| JP | 06-197703 A | 7/1994 |
| JP | 2000/103740 A | 4/2000 |
| RU | 2211048 C1 | 8/2003 |
| WO | WO-93/15740 A1 | 8/1993 |
| WO | WO-96/05160 A1 | 2/1996 |
| WO | WO-96/34601 A1 | 11/1996 |
| WO | WO-97/08960 A1 | 3/1997 |
| WO | WO-98/44808 A2 | 10/1998 |
| WO | WO-98/47392 A1 | 10/1998 |
| WO | WO-99/30701 A1 | 6/1999 |
| WO | WO-99/45792 A1 | 9/1999 |
| WO | WO-01/10901 A2 | 2/2001 |
| WO | WO-01/24787 A1 | 4/2001 |
| WO | WO-02/085831 A1 | 10/2002 |
| WO | WO-03/013268 A1 | 2/2003 |
| WO | WO-03/049726 A1 | 6/2003 |
| WO | WO-03/066583 A1 | 8/2003 |
| WO | WO-03/094908 A1 | 11/2003 |
| WO | WO-2004/016099 A1 | 2/2004 |
| WO | WO-2004/016214 A2 | 2/2004 |
| WO | WO-2004/019929 A1 | 3/2004 |
| WO | WO-2004/039171 A1 | 5/2004 |
| WO | WO-2005/079143 A2 | 9/2005 |
| WO | WO-2005/099478 A1 | 10/2005 |
| WO | WO-2006/034570 A1 | 4/2006 |
| WO | WO-2006/120494 A1 | 11/2006 |
| WO | WO-2006/120565 A2 | 11/2006 |
| WO | WO-2006/120567 A2 | 11/2006 |
| WO | WO-2007/007198 A1 | 1/2007 |
| WO | WO-2007/011330 A1 | 1/2007 |
| WO | WO-2007/043046 A2 | 4/2007 |
| WO | WO-2007/112587 A1 | 10/2007 |
| WO | WO 2007112587 A1 * 10/2007 .............. A23K 1/16 |

(56) References Cited

FOREIGN PATENT DOCUMENTS

| WO | WO-2009/052629 A1 | 4/2009 |
|---|---|---|
| WO | WO-2010/124391 A1 | 11/2010 |
| WO | WO-2010/124392 A1 | 11/2010 |
| WO | WO-2011/103464 A1 | 8/2011 |

OTHER PUBLICATIONS

Burton et al., "beta-Carotene autoxidation: oxygen copolymerization, non-vitamin A products, and immunological activity," Can J Chem. 92(4):305-16 (2014).
Burton et al., "Discovery and characterization of carotenoid-oxygen copolymers in fruits and vegetables with potential health benefits," J Agric Food Chem. 64(19):3767-77 (2016).
Duquette et al., "Anti-inflammatory effects of retinoids and carotenoid derivatives on caspase-3-dependent apoptosis and efferocytosis of bovine neutrophils," Am J Vet Res. 75(12):1064-75 (2014).
Johnson, et al., "Treatment of Seborrheic Dermatitis," American Family Physician, <http://www.aafp.org/afp/2000/0501/p2703.html>, retrieved Jun. 18, 2015 (6 pages).
Johnston et al., "Biologically active polymers from spontaneous carotenoid oxidation: a new frontier in carotenoid activity," PLoS One. 9(10):e111346 (2014).
Office Action for Canadian Patent Application No. 2,771,204, dated Apr. 8, 2016 (5 pages).
Office Action for Chilean Patent Application No. 2012-002309, dated Apr. 20, 2015 (23 pages).
Shojadoost et al., "The successful experimental induction of necrotic enteritis in chickens by Clostridium perfringens: a critical review," Vet Res. 43:74 (2012) (12 pages).
U.S. Appl. No. 08/527,039, Burton et al.
Alaoui-Jamali et al., "In vivo reversal of doxorubicin resistance by a new tiapamil analog Ro11-2933," J Pharmacol Exp Ther. 264(3)1 299-1304 (1993).
Alija et al., "Cytotoxic and genotoxic effects of beta-carotene breakdown products on primary rat hepatocytes," Carcinogenesis. 25(5):827-831 (2004).
Anonymous, "Vitamin A, tumor initiation and tumor promotion," Nutr Rev. 37(5):153-6 (1979).
Armand et al., "Specificity of the phase I trial for cytotoxic drugs in oncology," Fundam Clin Pharmacol. 4 Suppl 2:197s-204s (1990).
Blount et al., "Carotenoid modulation of immune function and sexual attractiveness in zebra finches," Science. 300(5616):125-7 (2003).
Brooks et al., Recent developments in the chemistry, biochemistry, geochemistry and post-tetrad ontogeny of sporopollenins derived from pollen and spore exines. *Pollen Development and Physiology.* J. Heslop-Harris, Butterworths, London, 99-114 (1971).
Brouwer et al., "A new synthesis of 4-OR*-3-penten-1-ynes (C5-fragment) as a tool for the preparation of vitamin A," J Royal Netherlands Chem Soc. 98: 316-320 (1979).
Brown et al., "New anticancer agents," Cancer Chemother Biol Response Modif. 13:115-55 (1992).
Burton et al., "Beta-carotene: an unusual type of lipid antioxidant," Science. 224(4649):569-73 (1984).
Chew, "Role of carotenoids in the immune response," J Dairy Sci. 76(9):2804-2811 (1993).
Clark et al., "Retinoic acid oxidation at high oxygen pressures: evidence for spin-forbidden direct addition of triplet molecular oxygen," J Am Chem Soc. 119(40):9560-9561 (1997).
Communication from the European Patent Office for European Application No. 05736675.9, dated Feb. 2, 2010 (5 pages).
Communication from the European Patent Office for European Application No. 10769196.6, dated May 31, 2013 (5 pages).
Communication from the European Patent Office for European Patent Application No. 08842588.9, dated Feb. 19, 2013 (6 pages).
Database Biosis for PREV200300291110, "Addition of beta-ionone to the diet fails to affect growth performance in female broiler chickens," (2003) (1 page).
Deming et al., "Mammalian carotenoid absorption and metabolism," Pure Appl Chem. 71(12):2213-2223 (1999).
El-Tinay et al., "Oxidation of beta-carotene. Site of initial attack," J Org Chem. 35(7):2290-2293 (1970).
English translation of Unfavorable Patentability Opinion for Brazilian Application No. PI 0516202-5, received Jan. 20, 2015 (4 pages).
Examination Report for Australian Patent Application No. 2010242502, dated Jan. 21, 2015 (5 pages).
Extended European Search Report and Search Opinion for European Application No. 10769196.6, dated Sep. 27, 2013 (6 pages).
Extended European Search Report for European Application No. 05791352.7, dated Feb. 14, 2008 (5 pages).
Extended European Search Report for European Application No. 08842588.9, dated Jun. 28, 2012 (10 pages).
Extended European Search Report for European Patent Application No. 11745354.8, dated May 2, 2014 (8 pages).
FAO, "Fish feeds and feeding," <ftp://ftp.fao.org/fi/cdrom/fao_training/FAO_Training/General/x6709e/x6709e10.htm, retrieved on Mar. 19, 2015 (45 pages).
First Examination Report for Indian Application No. 3064/CHENP/2010, dated Jul. 30, 2014 (3 pages).
Giuliani et al., "Preliminary observations with an ointment containing tretinoin (retinoic acid), salicylic acid, sulfur, betamethasone, camphor and allantoin in hyperkeratotic dermatosis," Chronica Dermatologica. 5:581-594 (1974).
Hardman et al., .Principles of therapeautics. *Goodman & Gilman's the Pharmacological Basis of Therapeutics.* 9th Edition. 51, 57-8 (1996).
Hawkins et al., "New anticancer agents: taxol, camptothecin analogs, and anthrapyrazoles," Oncology. 6(12):17-23 (1992).
Hill et al., "Retinoids and cancer prevention," Annu Rev Nutr. 12:161-181 (1992).
Hong et al., "Recent advances in chemoprevention of cancer," Science. 278(5340):1073-7 (1997).
Hoskinson et al., "Age-related changes in mitogen-induced lymphocyte proliferation and polymorphonuclear neutrophil function in the piglet," J Anim Sci. 68(8):2471-2478 (1990).
Hunter et al., "The oxidation of beta-carotene in solution by oxygen," J Chem Soc. Jan. 1-4, 1947.
International Preliminary Report on Patentability and Written Opinion for International Application No. PCT/CA2010/000671, dated Nov. 1, 2011 (10 pages).
International Preliminary Report on Patentability and Written Opinion in International Patent Application No. PCT/US2011/025481, dated Aug. 21, 2012 (13 pages).
International Preliminary Report on Patentability for International Application No. PCT/CA2005/001458, dated Feb. 7, 2007 (6 pages).
International Preliminary Report on Patentability for International Application No. PCT/CA2008/001879, dated Apr. 27, 2010 (8 pages).
International Search Report and Written Opinion for International Application No. PCT/CA2010/000671, dated Jul. 14, 2010 (14 pages).
International Search Report for International Application No. PCT/CA2005/001458, dated Jan. 3, 2006 (3 pages).
International Search Report for International Application No. PCT/CA2008/001879, dated Feb. 2, 2009 (6 pages).
Iwan'ska et al., "Carotenoids content of green forages and preserved feeds," Acta Acad Agri Ac Tech Olstenesis Zootechnica. 47:117-28 (1997) retrieved from CABI Abstracts. (Abstract only) (2 pages).
Kanasawud et al., "Mechanism of formation of volatile compounds by thermal degradation of cartenoids in aqueous medium. 2. lycopene degradation," J Agric Food Chem. 38:1238-1242 (1990).
Kiefer et al., "Identification and characterization of a mammalian enzyme catalyzing the asymmetric oxidative cleavage of provitamin A," J Biol Chem. 276(17):14110-14116 (2001).
Kim et al., "Dietary lutein stimulates immune response in the canine," Vet Immunol Immunopathol. 74(3-4):315-27 (2000).
Krinsky et al., "Actions of carotenoids in biological systems," Annu Rev Nutr. 13:561-587 (1993).

(56) References Cited

OTHER PUBLICATIONS

Lee et al., "Addition of beta-ionone to the diet fails to affect growth performance in female broiler chickens," Anim Feed Sci Technol. 106:219-223 (2003).
Loberto et al., "*Staphylococcus* spp. in the oral cavity and periodontal pockets of chronic periodontitis patients," Brazilian Journal of Microbiology 35:64-8 (2004).
Magnadóttir, "Innate immunity of fish (overview)," Fish Shellfish Immunol. 20(2):137-51 (2006).
Martin et al., "Chemistry of carotenoid oxidation and free radical reactions," Pure Appl Chem. 71(12):2253-2262 (1999).
Marty et al., "Degradation of trans-beta-carotene during heating in sealed glass tubes and extrusion cooking," J Food Sci. 51(3):698-702 (1986).
Marty et al., "Degradation products of trans-beta-carotene produced during extrusion cooking," J Food Sci. 53(6):1880-1886 (1988).
Mathews-Roth, "Carotenoids and cancer prevention: experimental and epidemiological studies," Pure Appl Chem. 57(5):717-22 (1985).
Medical News Today, "Chemaphor announces positive results of pilot canine clinical trial of an Oximunol™ supplement," dated Feb. 2, 2010, <http://www.medicalnewstoday.com/articles/177855.php>, retrieved on Jun. 9, 2010 (1 page).
Mordi et al., "Exploratory study of beta-carotene autoxidation," Tetrahedron Lett. 32(33):4203-6 (1991).
Mordi et al., "Oxidative degradation of beta-carotene and beta-apo-8'-carotenal," Tetrahedron. 49(4):911-928 (1993).
Morganti et al., "Protective effects of oral antioxidants on skin and eye function," Skinmed. 3(6):310-6 (2004).
Office Action for Chinese Application No. 200880122743.9, dated Jul. 20, 2011 (17 pages).
Office Action for Japanese Application No. 2010-530236, dated Jun. 18, 2013 (8 pages).
Office Action for Japanese Application No. 2010-530236, dated Sep. 2, 2014 (7 pages).
Okajima et al., "Biofilm formation by *Staphylococcus epidermidis* on intraocular lens material," Invest Ophthalmol Vis Sci. 47(7):2971-5 (2006).
Onyewu et al., "Characterization of beta-carotene thermal degradation products in a model food system," J Am Oil Chem Soc. 63(11):1437-1441 (1986).
Oyler et al., "Characterization of autoxidation products of retinoid acid," Tetrahedron 45(24):7679-7694 (1989).
Peto et al., "Can dietary beta-carotene materially reduce human cancer rates?," Nature. 290(5803):201-8 (1981).
Ramos-Gomez et al., "Sensitivity to carcinogenesis is increased and chemoprotective efficacy of enzyme inducers is lost in nrf2 transcription factor-deficient mice," Proc Natl Acad Sci USA. 98(6):3410-3415 (2001).
Rudnic et al., Oral Solid Dosage Forms. *Remington: The Science and Practice of Pharmacy*. Gennaro, 858-61 (2000).
Russell, "The enigma of beta-carotene in carcinogenesis: what can be learned from animal studies," J Nutr. 134(1):262S-268S (2004).
Sciarra et al., Aerosols. *Remington: The Science and Practice of Pharmacy*. Gennaro, 963 (2000).
Supplementary European Search Report for European Application No. 05736675.9, dated Sep. 18, 2009 (3 pages).
Tacon, "The nutrition and feeding of farmed fish and shrimp. A training manual: Feeding methods—complete diet feeding," FAO Corporate Document Repository Jun. 1987, <http://www.fao.org/docrep/field/003/ab467e/ab467e.htm> retrieved on Aug. 30, 2014 (27 pages).
Talalay et al., "Importance of phase 2 gene regulation in protection against electrophile and reactive oxygen toxicity and carcinogenesis," Adv Enzyme Regul. 43:121-134 (2003).
Talalay, "Chemoprotection against cancer by induction of phase 2 enzymes," Biofactors. 12(1-4):5-11 (2000).
Trosko et al., "Gap junctions as targets for cancer chemoprevention and chemotherapy," Curr Drug Targets 3(6):465-482 (2002) (17 pages).
Verma et al., "Inhibition of skin tumor promotion by retinoic acid and its metabolite 5,6-epoxyretinoic acid," Cancer Res. 40(7):2367-71 (1980).
Wang, "Can smoke-exposed ferrets be utilized to unravel the mechanisms of action of lycopene?," J Nutr. 135(8):2053S-2056S (2005).
Webster's New Collegiate Dictionary. Merriam-Webster (ed.), 49 (1977).
Weiss et al., "New anticancer agents," Cancer Chemother Bial Reponse Modif. 14:118-28 (1993).
Wikipedia, "Polysorbate 80," <http://en.wikipedia.org/wiki/Polysorbate_80>, retrieved on Nov. 20, 2013 (4 pages).
Extended European Search Report for European Application No. 16785701.0, dated Aug. 21, 2018 (6 pages).
International Search Report for International Application No. PCT/CA2016/050226, dated May 20, 2016 (5 pages).
Search Report and Written Opinion for Singapore Application No. 11201708728S, dated Oct. 23, 2018 (8 pages).
Written Opinion for International Application No. PCT/CA2016/050226, dated May 20, 2016 (7 pages).

\* cited by examiner

Figure 2
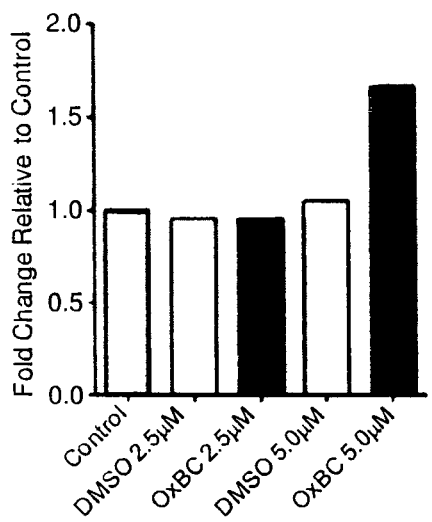
Fig. 2A
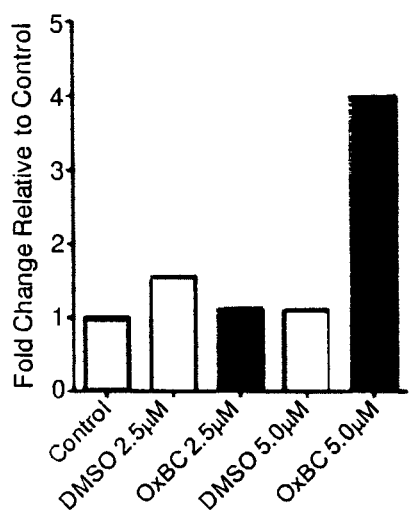
Fig. 2B
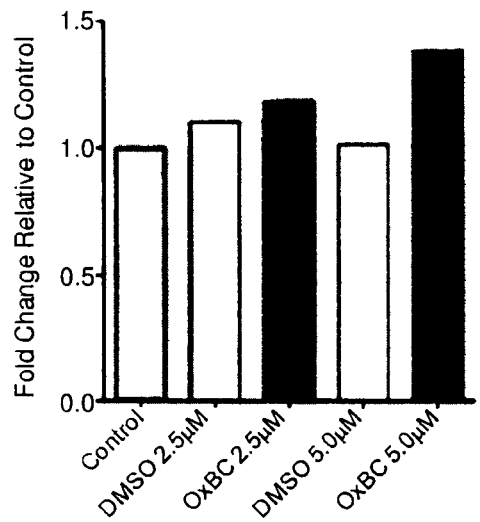
Fig. 2C

Figure 3
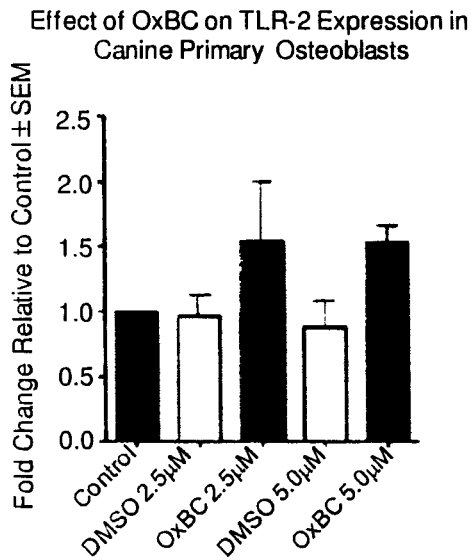
Fig. 3A
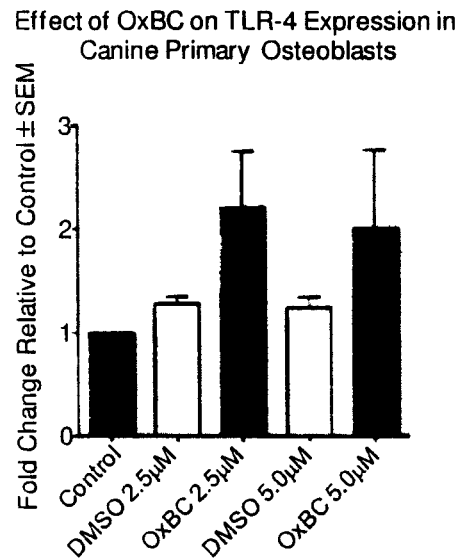
Fig. 3B
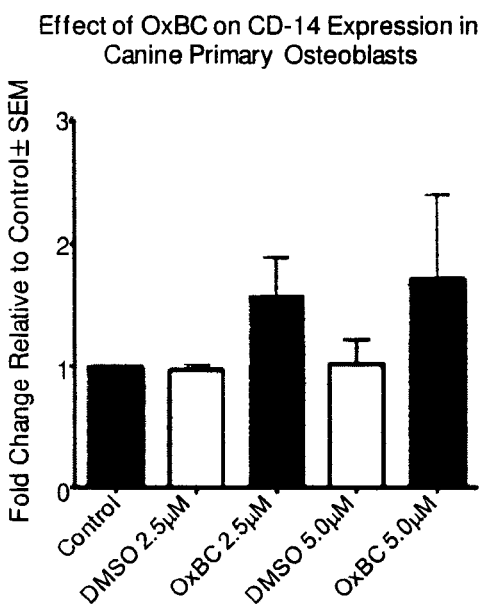
Fig. 3C

Figure 4
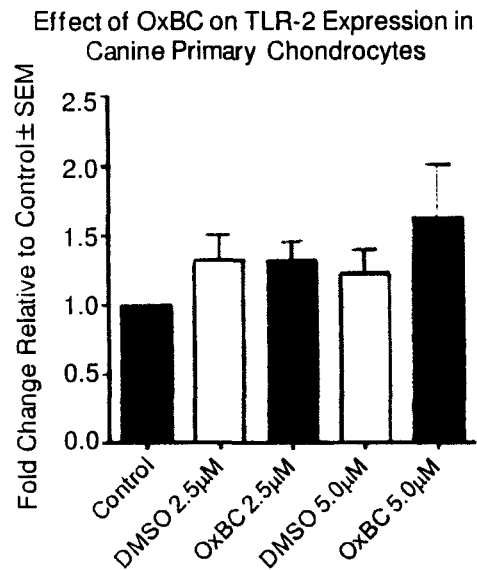
Fig. 4A
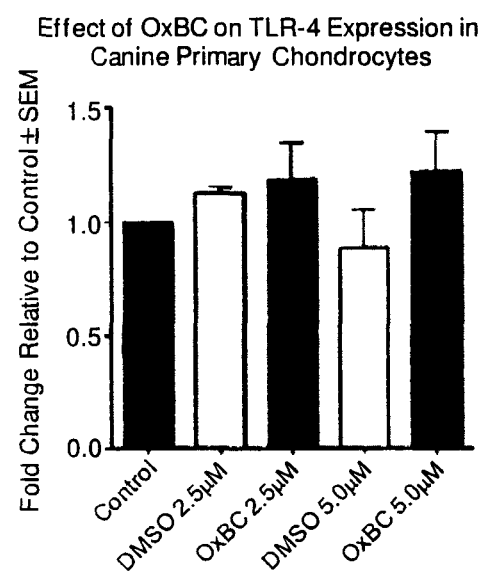
Fig. 4B

Figure 6
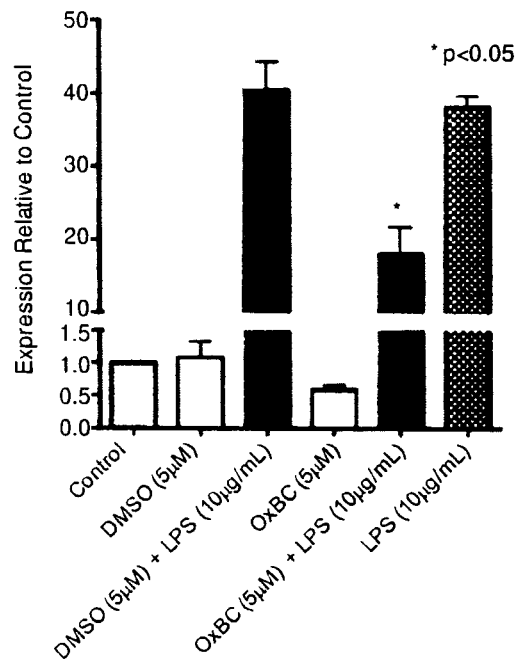
Fig. 6A
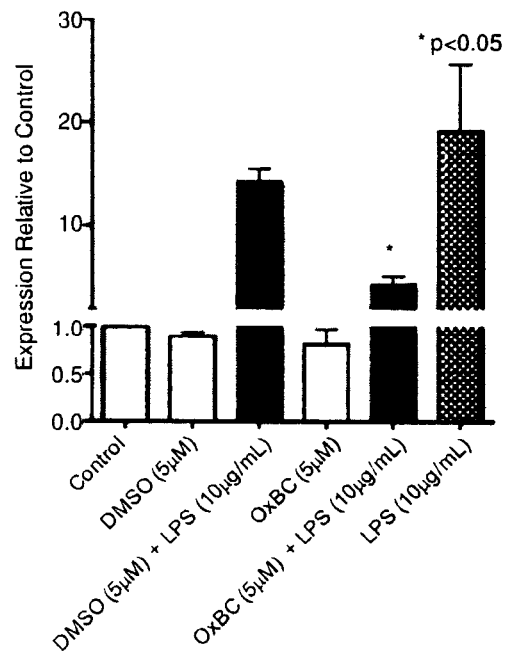
Fig. 6B

METHODS AND COMPOSITIONS FOR IMPROVING THE HEALTH OF ANIMALS

CROSS-REFERENCE TO RELATED APPLICATIONS

This application is the U.S. National Stage of International Application No. PCT/CA2010/000671, filed on Apr. 30, 2010, which claims the benefit of U.S. Provisional Application Ser. No. 61/174,259, filed Apr. 30, 2009.

BACKGROUND OF THE INVENTION

The invention relates to the use of carotenoid oxidation products for improving the health of an animal.

According to the American Pet Products Manufacturers Association's National Pet Owners Survey (NPOS), pets occupied 69 million U.S. households in 2006. This corresponds to 73 million dogs and 90 million cats. This number has increased from 2002 where 64 million households had pets. Furthermore, the State of the American Pet Survey revealed that 75% of pet owners state that their pet is a member of the family, and that maintaining optimal health is their top priority when caring for their pet.

Elderly pets often become frail in their last few years of life, often having a poor coat condition, digestive system problems, joint stiffness, energy loss, and/or reduced activity levels.

For example, the connective tissues of animals are constantly subject to stresses and strains from mechanical forces that can result in afflictions, such as arthritis (both rheumatoid and osteoarthritis), joint inflammation and stiffness. This is particularly true as animals age. The underlying causes of rheumatoid arthritis and/or osteoarthritis are different such that rheumatoid arthritis is characterized as an autoimmune disease affecting both the joints and systemic immune functions, whereas osteoarthritis results from deterioration of the articular cartilage which may result in local inflammation of the joints. While a greater portion of humans with arthritis have rheumatoid arthritis, most of the arthritis occurring in companion animals is osteoarthritis. In dogs, osteoarthritis is a disorder of the synovial joints which is characterized by degeneration of the articular cartilage and by formation of new bone at the joint margins. Hardening of the underlying subchondral bone may also be a feature of osteoarthritis and in some cases, a variable degree of synovial inflammation may be present at some time during the progression of the disease. The selective breeding of companion and domestic animals has inadvertently led to the propagation of many autoimmune and inflammatory diseases such that twenty-percent of the canine population greater than one year old is reported to have some degree of arthritis.

There is a need for new methods and compositions for improving the health and well being of animals, such as increasing joint mobility, increasing activity, and improving coat quality.

SUMMARY OF THE INVENTION

The invention provides compositions and methods for the administration of oxidatively transformed carotenoid and components thereof. The compositions can be useful for improving the health of an animal.

In a first aspect, the invention features a method of increasing joint mobility of an animal in need thereof by administering to the animal a composition including oxidatively transformed carotenoid, or a fractionated component thereof, in an amount sufficient to increase the joint mobility.

The invention also features a method of increasing the activity level of an animal by administering to the animal a composition including oxidatively transformed carotenoid, or a fractionated component thereof, in an amount sufficient to increase the activity level.

The invention further features a method of improving the coat quality of an animal by administering to the animal a composition including oxidatively transformed carotenoid, or a fractionated component thereof, in an amount sufficient to improve the coat quality.

The invention features a method of maintaining the coat quality of an animal by administering to the animal a composition including oxidatively transformed carotenoid, or a fractionated component thereof, in an amount sufficient to maintain or improve the coat quality.

The invention also features a method of reducing discoloration in an eye of an animal by administering to the animal a composition comprising oxidatively transformed carotenoid, or a fractionated component thereof, in an amount sufficient to reduce said discoloration.

In one embodiment of the above methods the composition is administered daily. For example, from 0.1 mg/kg body weight to 2 mg/kg body weight of oxidatively transformed carotenoid, or a fractionated component thereof, can be administered to the animal daily. In certain embodiments from 0.05 mg/kg to 1 mg/kg; 0.1 mg/kg to 3 mg/kg; 0.2 mg/kg to 1.5 mg/kg; 0.3 mg/kg to 2 mg/kg; 0.3 mg/kg to 1 mg/kg; 0.1 mg/kg to 1 mg/kg; 0.1 mg/kg to 0.8 mg/kg; 0.2 mg/kg to 1.2 mg/kg; or 0.25 mg/kg to 0.75 mg/kg of oxidatively transformed carotenoid, or a fractionated component thereof, is administered daily. The oxidatively transformed carotenoid, or a fractionated component thereof, can be mixed with food and administered orally to said animal. The food can be, without limitation, a wet animal food, a semi-moist animal food, a dry animal food, a kibble, a chew, a tablet, or a soft edible treat. Alternatively, the oxidatively transformed carotenoid, or a fractionated component thereof, can be administered to said animal as an oral supplement (e.g., formulated as a palatable paste or gel).

In certain embodiments of the above methods, the animal is a companion animal (e.g., a dog, a cat, a horse, or any other companion animal described herein).

In another embodiment of the above methods, the animal a mature animal, an animal that is elderly, or an animal that exhibits signs of aging (i.e., lethargy, immobility, or an unhealthy coat having dry, brittle, and/or loose hair in the coat).

In a related aspect, the invention features a comestible solid composition in unit dosage form including from 2 mg to 130 mg of oxidatively transformed carotenoid, or a fractionated component thereof, and formulated to be palatable to canines. In certain embodiments, the unit dosage form includes from 1 mg to 200 mg; 1 mg to 100 mg; 1 mg to 75 mg; 5 mg to 150 mg; 5 mg to 75 mg; 10 mg to 200 mg; 10 mg to 100 mg; 10 mg to 75 mg; 20 mg to 200 mg; 20 mg to 100 mg; or 30 mg to 150 mg of oxidatively transformed carotenoid, or a fractionated component thereof.

The invention also features a comestible solid composition in unit dosage form including from 0.25 mg to 14 mg of oxidatively transformed carotenoid, or a fractionated component thereof, and formulated to be palatable to felines. In certain embodiments, the unit dosage form includes from 0.25 mg to 14 mg; 0.1 mg to 20 mg; 0.1 mg to 10 mg; 0.25 mg to 10 mg; 0.5 mg to 14 mg; 0.5 mg to 10 mg; 0.75 mg to 14 mg; 0.75 mg to 10 mg; 1 mg to 14 mg; 1 mg to 10 mg;

2 mg to 14 mg of oxidatively transformed carotenoid, or a fractionated component thereof.

The invention also features a comestible solid composition in unit dosage form including from 39 mg to 1,500 mg of oxidatively transformed carotenoid, or a fractionated component thereof, and palatable to equines. In certain embodiments, the unit dosage form includes from 20 mg to 2,000 mg; 20 mg to 1,500 mg; 20 mg to 1,000 mg; 50 mg to 2,000 mg; 50 mg to 1,500 mg; 50 mg to 1,000 mg; 100 mg to 2,000 mg; 100 mg to 1,500 mg; 100 mg to 1,000 mg; 250 mg to 2,000 mg; 250 mg to 1,500 mg; or 250 mg to 1,000 mg of oxidatively transformed carotenoid, or a fractionated component thereof.

In an embodiment of any of the comestible solid dosage compositions, the unit dosage form is a kibble, a chew, a tablet, or a soft edible treat.

The invention further features a palatable comestible gel or paste including from 2 mg/tablespoon to 750 mg/tablespoon of oxidatively transformed carotenoid, or a fractionated component thereof. In certain embodiments, the comestible gel or paste includes from 1 mg/tablespoon to 750 mg/tablespoon; 5 mg/tablespoon to 750 mg/tablespoon; 5 mg/tablespoon to 500 mg/tablespoon; 1 mg/tablespoon to 250 mg/tablespoon; 5 mg/tablespoon to 250 mg/tablespoon; 10 mg/tablespoon to 500 mg/tablespoon; 10 mg/tablespoon to 100 mg/tablespoon; 5 mg/tablespoon to 100 mg/tablespoon; or 25 mg/tablespoon to 250 mg/tablespoon of oxidatively transformed carotenoid, or a fractionated component thereof.

The invention features a kit including (i) dog food, (ii) oxidatively transformed carotenoid, or a fractionated component thereof, and (iii) instructions for feeding a dog an amount of the composition containing from 2 mg to 130 mg of the oxidatively transformed carotenoid, or a fractionated component thereof. The kit can further include instructions for feeding the dog daily. The dog food can be, for example, a dry dog food, a wet dog food, or a semi-moist dog food.

The invention also features a kit including (i) cat food, (ii) oxidatively transformed carotenoid, or a fractionated component thereof, and (iii) instructions for feeding a cat an amount of the composition containing from 0.25 mg to 14 mg of the oxidatively transformed carotenoid, or a fractionated component thereof. The kit can further include instructions for feeding the cat daily. The cat food can be, for example, a dry cat food, a wet cat food, or a semi-moist cat food.

In an embodiment of any of the above kits, the kit is provided in a single serving container (e.g., a pouch, a packet, or a can).

In any of the above methods, comestible compositions, and kits, the composition includes fractionated oxidatively transformed carotenoid.

In any of the above methods, comestible compositions, and kits the composition includes unfractionated oxidatively transformed carotenoid.

By "animal" is meant any animal including, without limitation, humans, dogs, cats, horses, sheep, swine, cattle, poultry, and fish.

By an "amount sufficient" is meant the amount of oxidatively transformed carotenoid, or a fractionated component thereof, required to increase joint mobility, increase the activity level, or improve the coat quality. The effective amount of a composition of the invention used to practice the methods of the invention varies depending upon the manner of administration, the type of animal, body weight, and general health of the animal. Ultimately, the attending physician or veterinarian will decide the appropriate amount and dosage regimen. Such amount is referred to as an "amount sufficient."

As used herein, "carotenoid" refers to naturally-occurring pigments of the terpenoid group that can be found in plants, algae, bacteria, and certain animals, such as birds and shellfish. Carotenoids include carotenes, which are hydrocarbons (i.e., without oxygen), and their oxygenated derivatives (i.e., xanthophylls). Examples of carotenoids include lycopene; β-carotene; zeaxanthin; echinenone; isozeaxanthin; astaxanthin; canthaxanthin; lutein; citranaxanthin; β-apo-8'-carotenic acid ethyl ester; hydroxy carotenoids, such as alloxanthin, apocarotenol, astacene, astaxanthin, capsanthin, capsorubin, carotenediols, carotenetriols, carotenols, cryptoxanthin, decaprenoxanthin, epilutein, fucoxanthin, hydroxycarotenones, hydroxyechinenones, hydroxylycopene, lutein, lycoxanthin, neurosporine, phytoene, phytofluoene, rhodopin, spheroidene, torulene, violaxanthin, and zeaxanthin; and carboxylic carotenoids, such as apocarotenoic acid, β-apo-8'-carotenoic acid, azafrin, bixin, carboxylcarotenes, crocetin, diapocarotenoic acid, neurosporaxanthin, norbixin, and lycopenoic acid.

By "companion animal" is meant any domestic animal, including, without limitation, domesticated dogs, cats, horses, pigs, sheep, and cows.

As used herein "fractionated" refers to a composition containing the oligomeric material formed in the production of the oxidatively transformed carotenoid mixture. Methods of fractionating oxidatively transformed carotenoid mixtures into components are described in U.S. Pat. No. 5,475,006 and U.S. Ser. No. 08/527,039, each of which are incorporated herein by reference.

As used herein "oxidatively transformed carotenoid" refers to a carotenoid which has been reacted with up to 6 to 8 molar equivalents of oxygen, or an equivalent amount of oxygen from another oxidizing agent, resulting in a mixture of very low molecular weight oxidative cleavage products and a large proportion of oligomeric material (i.e., that component of the oxidatively transformed carotenoid having a median molecular weight of about 900 Daltons). The resulting reaction produces a mixture that includes molecular species having molecular weights ranging from about 100 to 8,000 Daltons. The oligomeric material is believed to be formed by the many possible chemical recombinations of the various oxidative fragments that are formed. Methods of making oxidatively transformed carotenoid are described in U.S. Pat. No. 5,475,006 and U.S. Ser. No. 08/527,039, each of which are incorporated herein by reference. As used herein, the term "OxBC" refers specifically to oxidatively transformed carotenoid derived from β-carotene.

The term "palatable" refers to at least 60% voluntary (free choice) acceptance or ingestion of a composition of the invention by a type of animal, as measured by a standard palatability test, such as acceptance testing, preference testing or consumption testing. The term "palatable to canines" refers to at least 60% voluntary (free choice) acceptance or ingestion of a composition of the invention by canines in a standard palatability test. The term "palatable to felines" refers to at least 60% voluntary (free choice) acceptance or ingestion of a composition of the invention by felines in a standard palatability test. The term "palatable to equines" refers to at least 60% voluntary (free choice) acceptance or ingestion of a composition of the invention by equines in a standard palatability test.

As used herein, the term "treating" refers to administering a composition for prophylactic and/or therapeutic purposes. To "prevent disease" refers to prophylactic treatment of an animal who is not yet ill, but who is susceptible to, or otherwise at risk of, a particular disease. To "treat disease" or use for "therapeutic treatment" refers to administering treatment to an animal already suffering from a disease to improve or stabilize the animal's condition. Thus, in the claims and embodiments, treating is the administration to an animal either for therapeutic or prophylactic purposes. As used herein, "at risk of" refers to animals prone to poor joint mobility, reduced activity levels, and/or poor coat quality.

By "maintaining or improving coat quality" is meant maintaining or improving the quality of an animal's coat using the methods of the invention in comparison to an animal of similar condition and age that is left untreated. Criteria for assessing coat quality can include (a) measuring shedding index of a test subject by collecting hair produced during a standardized brushing session (i.e., the hair is retained and weighed, and control and test subjects compared); and (b) subjective coat evaluations using trained panelists to subjectively evaluate coat condition by assessing shedding, dander, shine, uniformity, softness, and density.

By "increasing joint mobility" is meant increasing the joint mobility of an animal using the methods of the invention in comparison to an animal of similar mobility and age that is left untreated. Criteria for assessing joint mobility can include an orthopedic evaluation the degree of lameness, weight bearing, resistance to challenged weight bearing, rear leg extension, and visual inspection of an animal's ability to walk and/or trot. Joint angles and range of motion may also be determined by manual goniometric measurements. Additionally, force-plate analysis could be used to determine joint health.

By "increasing activity level" is meant increasing the activity level of an animal using the methods of the invention in comparison to an animal of similar activity and age that is left untreated.

Other features and advantages of the invention will be apparent from the following Detailed Description, the Drawings, and the Claims.

BRIEF DESCRIPTION OF THE DRAWINGS

FIG. 2 is a series of graphs showing the effect of OxBC on expression of immune receptors in canine primary plasma dendritic cells. Dendritic cells were incubated with the indicated concentrations of OxBC or vehicle control (DMSO) for 24 hours. Plasma membrane expression of toll-like receptor subtype-2 (TLR-2; FIG. 2A), toll-like receptor subtype-4 (TLR-4; FIG. 2B), and CD-14 (FIG. 2C) were determined by FACS analysis. Effects of OxBC are shown relative to untreated control cells. These results show that OxBC is able to up-regulate the abundance of pathogen sensing TLR-2, TLR-4 and CD-14receptors on the plasma membrane of dendritic cells, a primary effector cell type of the immune system.

FIG. 3 is a series of graphs showing the effect of OxBC on expression of immune receptors in canine primary osteoblasts. Cells were incubated with the indicated concentrations of OxBC or vehicle control (DMSO) for 24 hours. Plasma membrane expression of toll-like receptor subtype-2 (TLR-2; FIG. 3A), toll-like receptor subtype-4 (TLR-4; FIG. 3B), and CD-14 (FIG. 3C) were determined by FACS analysis. Effects of OxBC are shown relative to untreated control cells. These results show that OxBC is able to up-regulate the abundance of pathogen sensing TLR-2, TLR-4 and CD-14 receptors on the plasma membrane of canine osteoblasts. Osteoblasts are not primary effectors of the immune system, however, they may play a secondary role in innate immunity by detecting invading pathogens.

FIG. 4 is a series of graphs showing the effect of OxBC on expression of immune receptors in canine primary chondrocytes. Cells were incubated with the indicated concentrations of OxBC or vehicle control (DMSO) for 24 hours. Plasma membrane expression of toll-like receptor subtype-2 (TLR-2; FIG. 4A) and toll-like receptor subtype-4 (TLR-4 ; FIG. 4B) were determined by FACS analysis. Effects of OxBC are shown relative to untreated control cells. These results show that OxBC is able to up-regulate the abundance of pathogen sensing TLR-2, TLR-4 and CD-14 receptors on the plasma membrane of canine chondrocytes. Chondrocytes, like osteoblasts, are not primary effectors of the immune system, however, they may play a secondary role in innate immunity by detecting invading pathogens.

FIG. 6 is a series of graphs showing the suppressive effect of OxBC on chemokine expression in naïve and challenged canine primary fibroblasts. Fibroblasts were pre-treated with OxBC or vehicle control (DMSO) for 24 hours. Following pre-treatment cells were challenged by exposure to bacterial lipopolysaccharide (LPS) for 4 hours. Chemokine expression was measured using quantitative real-time PCR with total RNA. Results show that in the context of an LPS challenge (dark bars) OxBC has a significant suppressive effect on the level of MCP-1 (FIG. 3A) and RANTES (FIG. 3B) gene-expression. Vehicle control (DMSO) showed no significant effect on chemokine expression. For LPS challenge experiments (dark bars) the suppressive effect of OxBC was evaluated relative to cells treated with LPS alone using Student's t-test. OxBC treatment of naïve fibroblasts (light bars) resulted in a trend towards decreased MCP-1 and RANTES expression. The effects of OxBC on chemokine expression in naïve cells were evaluated relative to untreated control cells.

DETAILED DESCRIPTION

Figure 1:
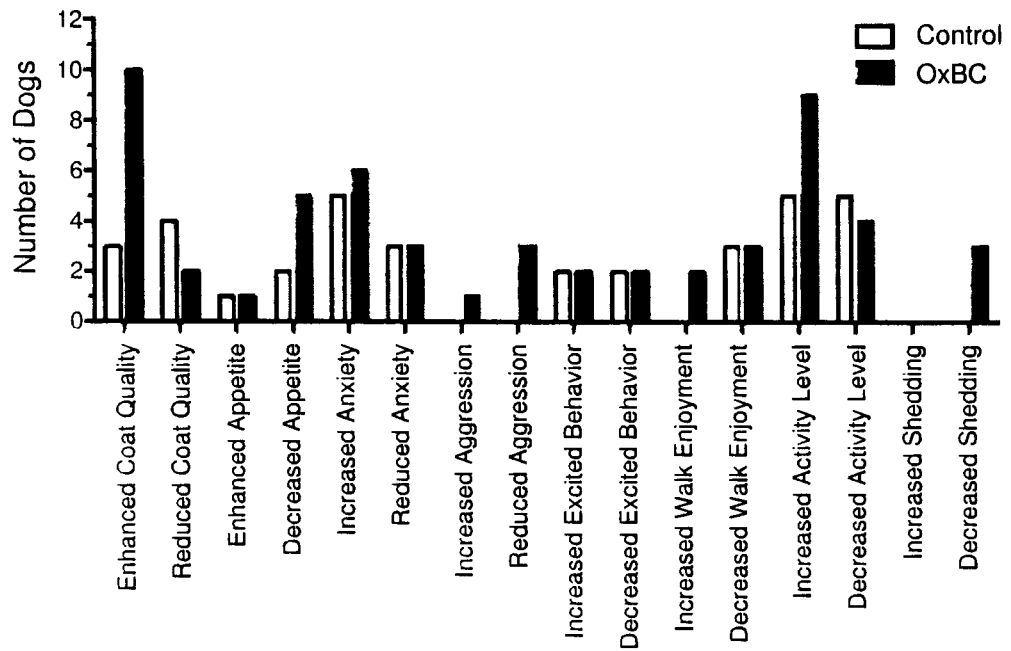
FIG. 1 is a chart depicting the distribution of outcomes based on owners' comments in Control and OxBC-Treated (0.5 mg/kg body weight) dogs after a 6-month treatment period (see Example 2).

The invention provides compositions and methods for the administration of oxidatively transformed carotenoid and components thereof. The compositions can be useful for improving the health and well being of an animal. Specifically, the compositions can be useful for increasing joint mobility, increasing activity, and improving coat quality in an animal. The compositions can be formulated in a comestible unit dosage form or be formulated into a comestible gel or paste.

The compositions of the invention can include one or more palatability improving agents including, without limitation dairy-based flavoring agents, a mixture of a natural herbs and spices, artificial egg flavor, artificial meat flavor, artificial chicken flavor, artificial fish flavor, yeast flavor, or combinations thereof. Such palatability improving agents are known in the art. For example, the palatability improving agents can include hydrolyzed vegetable protein, blends of natural flavoring and spices (sold as Sirius Stuff™ and Dog Bone marinade, manufactured by Dirigo Corp.); vegetarian beef, vegetarian bacon, or roast garlic (manufactured by Geneva Ingredients, Inc.); blends of dried skim milk, malted milk, whey and other products (sold as All diary Blend™); yeast flavoring (sold as Brewtech™ Dried Brewer's Yeast); blends of animal proteins and fat formulated to replace whole egg (sold as Eggsact™); blends of white and yellow cheese product powders, and cheese rind (sold as Cheese Plus Cheese™, manufactured by International Ingredients Corp.); peanut butter and artificial chicken (manufactured by Bush Bake Allan Americas); and/or artificial beef (manufactured by Pharmachemie at Syracuse, Nebr.).

Pet Food

Pet foods formulation with oxidatively transformed carotenoid, or a fractionated component thereof, according to the invention may be in any suitable form, for example a powder, a dried kibble, or pellet or other dried form, extruded form, semi-moist or wet form, such as a chunk or loaf or pudding. It may be chilled or provided as a shelf stable product.

While compositions of any consistency or moisture content are contemplated, preferably the food compositions of the present invention may be, for example, a wet, semi-moist, or dry animal food composition. "Wet" food refers to food that has a moisture content of about 70 to 90%. "Semi-moist" food refers to food that has a moisture content of about 15% to 40%. "Dry" food refers to compositions about 5% to 15% moisture content and is often manufactured in the form of small bits or kibbles. Also contemplated herein are compositions that may comprise components of various consistency as well as components that may include more than one consistency, for example, soft, chewy meat-like particles as well as kibble having an outer cereal component and an inner cream component as described in, e.g., U.S. Pat. No. 6,517,877. The kibble may then be dried and optionally coated with one or more topical coatings known by those skilled in the art, for example, flavors, fats, oils, powders, and the like. The compositions of the present invention can be prepared using conventional manufacturing methods.

Comestible Unit Dosage Forms

Oxidatively transformed carotenoid or a fractionated component thereof can be incorporated into a comestible solid composition in unit dosage form (i.e., a chew, a kibble, a chewable tablet, or a soft edible treat).

Chew Products

One of the main attributes of chew products is a toughness and flexibility to the point where it takes an animal (i.e., a dog) a long time (e.g., more than 30 seconds or 1 minute) to consume the product. Numerous pig and cattle body parts such as bones, ears, hooves and skin have been used to produce palatable dog treats with extended chew times. A great majority of the chew style products are made from rawhide, an economical starting material, and include flavorings and/or fragrances to make the chew palatable to animals.

Methods for making chews are known in the art. For example, U.S. Pat. No. 2,988,045 describes processing rawhide into layers that can be shaped and dehydrated to produce a chew; U.S. Pat. No. 4,702,929 describes a method for extruding rawhide byproduct fraction, called spetches, with starch to form a chew in stick form; U.S. Pat. No. 5,047,231 describes the inclusion of an inorganic pyrophosphate salt in the rawhide to form a chew capable of reducing tartar accumulation; U.S. Pat. No. 6,223,693 describes a method of soaking rawhide in a humectant and soft edible binder to produce a flexible chew; U.S. Pat. No. 6,840,196 describes a multi-layered chew in which the inner layers are impregnated with a flavoring; U.S. Pat. No. 6,895,900 describes chew product made from a combination rawhide and pigskin; U.S. Pat. No. 6,886,497 describes a chew product made from rawhide or pigskin and infused with a flavoring; and U.S. Pat. No. 5,635,237 describes melting rawhide scraps inside of a twin-screw extruder to produce ropes that can be cut and tied to produce a formulated knotted rawhide bone. Vegetable-based and polymer-resin based chew products are also known in the art (see U.S. Pat. Nos. 6,821,538; 6,159,516; 6,110,521; 6,093,427; and 5,941,197). Many commercially successful chew products incorporate a meat fraction within the product to increase the palatability of the chew (see, e.g., U.S. Pat. Nos. 5,673,653; 6,277,420; 6,886,496). Oxidatively transformed carotenoid, or a fractionated component thereof, can be incorporated into any of the chew products described above.

Kibble Products

Kibbles are a dry or semi-moist comestible product made using a baking or heat extrusion process that forms the kibble under high temperature into any desired shape. Additives, such as antioxidants, nutrients, vitamins, minerals and the like, are commonly blended with the kibble ingredients prior to heating/forming, or coated onto the kibble after processing.

Methods for making kibble are well known in the art. For example, dry ingredients, including, animal protein sources, plant protein sources, grains, etc., are ground and mixed together. Moist or liquid ingredients, including fats, oils, animal protein sources, water, etc., are then added to and mixed with the dry ingredients. The mixture is then processed into kibbles. Kibble can be formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, and/or powders. Kibble also can be made from the dough using a baking process, rather than extrusion, wherein the dough is placed into a mold before dry-heat processing.

Oxidatively transformed carotenoid, or a fractionated component thereof, can be incorporated into a kibble product either prior to processing, or coated onto the kibble product after the kibble is formed.

Chewable Tablets

Oxidatively transformed carotenoid, or a fractionated component thereof, can be incorporated into a chewable tablet. For example, the oxidatively transformed carotenoid, or a fractionated component thereof, can be mixed with a binding agent and a palatbility enhancer and the mixture transferred to a tablet press and compressed into a tablet at an appropriate compression pressure. Methods for making palatable chewable tablets for delivery of therapeutic agents to companion animals are known in the art (see, for example, U.S. Patent Publication No. 20030190343 and U.S. Pat. No. 4,234,575).

Soft Edible Treats

Soft edible treats are comestible solid and semi-solid products which are flexible (i.e., with the consistency similar to that of a hot dog).

Soft edible treats include rubbery-textured dosage forms made from pectin, starch, or gelatin (i.e., a 'gummy bear' type formulation). Typically, starch produces a shorter (cleaner bite, less chewy) texture than gelatin. The ingredients of the composition can be combined, preferably by mixing in water that is heated sufficiently to form the gel, and can then be extruded, molded, or cut into the desired shapes by means that are well known in this field. The resulting gelled composition will typically be semi-solid. Such dosage forms including flavors and fragrances to enhance the palatability of the soft edible treat are known in the art (see, e.g., Gummy Bear BQ's chewy vitamin dog treats).

Oxidatively transformed carotenoid, or a fractionated component thereof, can be incorporated into any of the soft edible treat products described above.

Comestible Pastes and Gels

Oxidatively transformed carotenoid or a fractionated component thereof, can be incorporated into a comestible gel or paste.

For example, oxidatively transformed carotenoid or a fractionated component thereof, can be dispersed in an edible gel carrier. Suitable gelling agents include, without limitation, gum arabic, ghatti, tragacanth, guar, locust bean gum, agar, algin, carrageenan, pectin, chitin, gelatin, amylose, and amylopectin.

A comestible paste of the invention can be prepared from a variety of ingredients including, without limitation, a ground preparation of meat, fish, poultry, cheese, fruit, nut, vegetable, or combinations thereof. Additional ingredients may include oil, emulsifiers, anti-oxidants (e.g., butylated hydroxyanisole, butylated hydroxytoluene, tertiary butyl hydroquinone), natural preservatives, water, broth, juice, sweetener, and natural or artificial colors and flavorings, and gum arabic (acacia).

Methods for making comestible gels and pastes are known in the art (see, e.g., PCT Patent Publication Nos. WO2007/011330; WO 98/47392; WO2004/039171; and WO9945792). U.S. Pat. No. 7,001,889 and U.S. Patent Publication No. 20070298077 describe methods for preparing a paste for delivering a therapeutic substance within a comestible paste.

The following examples are put forth so as to provide those of ordinary skill in the art with a complete disclosure and description of how the methods and compositions claimed herein are performed, made, and evaluated, and are intended to be purely exemplary of the invention and are not intended to limit the scope of what the inventors regard as their invention.

Example 1

Oxidatively Transformed Carotenoid (OxBC) in Older Dogs

Seven privately-owned older dogs, age 8-15, received OxBC (0.5 mg/kg/day) as an oral supplement blended with cream cheese vehicle.

At the start of the study most dog-owners characterized their animals as lethargic with diminished desire for outdoor activity. Upon supplementation with OxBC for four months these owners reported that their dogs showed improved demeanor and were more eager to go outside and play. Improved coat quality as indicated by reduced shedding and a shinier appearance was an additional OxBC-benefit reported by some owners.

Following five months of receiving OxBC the dogs were taken off the supplement for seven weeks. During this seven-week period owners reported that their dog's desire for activity appeared to be returning towards pre-study levels. Upon restarting the OxBC supplement these same owners reported that their dogs once again responded positively showing increased active levels and improved mobility.

Example 2

Clinical Study of Oxidatively Transformed Carotenoid (OxBC) in Dogs

A clinical trial was conducted to evaluate the efficacy of carotenoid oxidation products in dogs using OxBC as a supplement. There were significant improvements in coat quality and shedding, as well as a trend towards improvement of walk enjoyment, in treated dogs compared to controls.

The clinical study consisted of a blinded, randomized study with two treatment groups. Forty-six dogs were recruited from the public. Dogs were randomly assigned to either treatment (0.5 mg OxBC/kg body weight in cream cheese) or placebo (cream cheese only) as they were enrolled, regardless of breed, age, sex and neuter status, and whether or not the animal had any medical conditions, was on any medications or was receiving any additional nutritional supplementation. The owner administered the treatment or placebo once daily for a period of six months. This study was conducted with the oversight and approval from the University of Prince Edward Island Animal Care Committee.

At the start of the trial, the participating dog owners completed an enrolment form, which detailed general information about the dog (i.e. breed, age, health status). The owners were then asked to fill out a questionnaire (Questionnaire 1) prior to the trial. At the end of the six-month trial period, owners were asked to fill out a second questionnaire (Questionnaire 2). The questionnaires asked the owners to rate their dog's behaviour, using numerical schemes, with respect to level and enjoyment of physical activity (walks), as well as their dog's appetite and coat quality. For Questionnaire 2, in addition to the numerical ranking, owners were asked to note any changes in the specific behaviours, appetite and coat quality over the six months of study participation. For each question, participants were given multiple response choices as well as an option to provide further detail.

Initial Mid-Study Results at Three Months:

In addition to completing questionnaires at the beginning and end of the study owners were contacted by phone or E-mail at the half-way point (3 months) to evaluate study progress and collect initial impressions of the OxBC supplement. During these mid-term evaluations the owners of several dogs receiving the OxBC treatment reported improvements in their animal, including increased mobility and energy levels, improved coat quality (i.e., improved coat from rough to shinny and silky), increased willingness to go for walks, and reduced pigmentation spots in the eyes (brown age spots). Notably, some dogs with observed improvement in mobility and energy levels had previously been characterized as lethargic by their owners due to arthritis, lameness due to cruciate ligament surgery, and other conditions causing immobility.

Final Clinical Trial Results at Six Months:

The outcomes in the final analysis of this study were obtained from two sources. The first were categorical in nature and were based on the owner's ranking or rating of specific behaviors, appetite, and coat appearance before and after the treatment period. The second set of outcomes consisted of the outcomes as modified according to specific comments provided by the owners. For example, the outcome "shedding" was derived from responses to the outcome "coat quality".

For each of the first set of outcomes seven variables were created consisting of the differences in responses between Questionnaire I and Questionnaire II. The general linear models procedure (Proc GLM) in the SAS software package (Statistical Analysis System for Personal Computers, Version 9, SAS Institute, Cary, N.C.) was then used to test the simple association between treatment and each of these difference variables. Outcome variables with a P-value<0.35 were then investigated further in multivariate models. Potential covariates (age, sex, weight category, adherence to treatment regimen, health and neuter status) were first tested for significance in a univariate model with each of the significant dependent variables. A liberal P-value of <0.20 was used for the initial inclusion of covariates in the full model. A manual backwards stepwise elimination process was then used to remove variables from the models with a P-value>0.05. Treatment was handled as a fixed effect. All relevant interaction terms were tested for significance. A final model was obtained when all interaction terms and variables in the model, with the exception of treatment, were significant at the 5% level. The effect of treatment was considered to be statistically significant in the final model of each of these outcomes, if the associated P-value was less than or equal to 0.10.

For each of the second set of outcomes, the proportions of treated and control dogs having an enhanced or reduced response following the treatment period were graphed (FIG. 1). Specific variables were then selected for Chi square analysis based on differences between proportion of Treated versus Control dogs and present knowledge of OxBC mode of action. A square root transformation was applied to the "enhanced coat quality" variable, and this variable was subjected to analysis using the GLM procedure. Weight, age, sex, neuter status, adherence to treatment regimen, supplements given and health status were then tested as covariates. Covariates were considered to be significant in the final model if P≤0.10.

Analysis of variance for the first set of outcomes for differences between Questionnaires 1 and 2 indicated a potential association between OxBC treatment and the outcome "walk enjoyment" (P<0.35). Therefore, this outcome was selected for further analysis using Proc GLM to assess the possible effect of covariates (sex, age, neuter status, weight category, adherence to treatment regime and health) on the observed association.

In univariate models, health status was found to be a significant predictor of "walk enjoyment" scores (P<0.05), however, this variable was not significant (P=0.30) when included in the full model and was thus removed. In the final model (which contained only treatment), the Treated dogs had a higher mean score for walk enjoyment than the Placebo group (two-sided P=0.15; one sided P=0.08,).

From the second set of outcomes, "enhanced coat quality", "decreased appetite", "increased activity level", and "decreased shedding" were selected for further analysis. Results of Chi square tests for differences in the proportions of Treated and Placebo dogs for each of these outcomes are shown in Table 1. There was a significant increase (P=0.05, one-tailed tests) in the proportion of treated dogs having enhanced coat quality and decreased shedding (P=0.04, one-tailed tests), compared to controls. Further analysis of the Enhanced Coat Quality outcome using GLM procedure and square root transformation indicated that treated dogs had significantly higher mean enhanced coat quality scores when controlling for weight (P<0.037).

TABLE 1

| Variable | Treatment | Proportion affected | P-value Two-tailed | P-value One-tailed |
|---|---|---|---|---|
| Enhanced coat quality | OxBC | 0.37 | 0.10 | 0.05 |
|  | Placebo | 0.16 |  |  |
| Decreased appetite | OxBC | 0.18 | 0.45 | 0.23 |
|  | Placebo | 0.11 |  |  |
| Increased activity level | OxBC | 0.30 | 0.51 | 0.25 |
|  | Placebo | 0.21 |  |  |
| Decreased shedding | OxBC | 0.11 | 0.07 | 0.04 |
|  | Placebo | 0.00 |  |  |

In addition to collecting data from formal questionnaires, owners were also given the opportunity to discuss their animal's health through an interview with the study co-ordinator. These discussions were held at the mid-term and end of the study. Mid-term discussions revealed three general trends for dogs receiving OxBC relative to the placebo group, namely: 1) increased activity levels, 2) increased willingness to go for walks, and 3) shinier coat appearance. Furthermore, final discussions held at the end of the study confirmed that positive effects reported at mid-term were sustained during the second half of the trial.

A case study conducted with OxBC with a single dog yielded positive results that strongly reflected the findings of the clinical trial. A male Tibetan terrier (age 14) was followed for a period of 18 months. The dog received OxBC (0.5 mg/kg body weight) in addition to its regular daily nutritional routine (which included glucosamine and vitamins) for the first eight months of the study, at which point OxBC was withdrawn for two-months. Administration of OxBC then was resumed for an additional eight months. Information on the dog's health status was obtained though personal examination of the dog by the coordinating veterinarian, personal communication between the owner and the veterinarian, and from owner responses to a series of standardized questions regarding the health of the animal.

The owner reported that prior to receiving the OxBC supplement the dog was lethargic, quiet, and unwilling to go for walks. However, following the first three months of supplementation with OxBC the dog's activity level rose and it was more willing to go on walks. After six months on the supplement the dog showed much higher activity levels, would routinely run during walks and had an overall healthier appearance. When the supplement was withdrawn for two months the owner reported that the dog returned to its prior lethargic state. Upon resuming the OxBC supplement the dog once again showed increased activity levels and willingness to go outside. The owner also reported that the dog's coat quality had improved over the course of the study, becoming thicker and shinier.

The key findings of the proof of concept clinical investigation are that OxBC supplementation leads to improved coat quality and activity levels in dogs and these findings are supported by the results of a case study with a single dog. In addition, no adverse effects have been reported for dogs receiving OxBC, confirming the safety of this product for use in dogs. These results highlight the potential for OxBC as a dietary health supplement for dogs and other companion animals.

All of the dogs participating in the studies of Examples 1 and 2 were reported to be receiving additional supplements for prolonged periods of up to several years before the OxBC studies began. These additional supplements included fish oil, glucosamine and various other anti-inflammatory products. The fact that OxBC is able to improve general animal health at the level of activity, joint mobility and coat quality in dogs that were already receiving supplements known to target these parameters is noteworthy. These observations suggest that OxBC's apparent ability to improve general animal health occurs by a mode of action that is distinct from other commonly used supplements.

Example 3

In Vitro Studies

Established cultures of canine osteoblasts, chondrocytes, and fibroblasts as well as isolated primary dendrictic cells and monocytes were used as model systems to evaluate OxBC-effects on canine immunity. Flow cytometry was used to assess the ability of OxBC to up-regulate expression of innate immune receptors and to enhance the activity of innate immune effector cells. A quantitative real-time PCR (QRT-PCR) approach was used to evaluate changes in the expression of regulators of inflammatory/immune response, which have been previously identified as potential contributors to or therapeutic targets in the pathology of arthritis.

Experimental Methods

Flow Cytometry: Canine osteoblasts, chondrocytes, or dendritic cells were seeded ($0.5 \times 10^5$-$1.0 \times 10^5$) onto 6 well plates 24 hours prior to treatment with OxBC. Cells were next treated with the indicated concentrations of OxBC or equivalent DMSO (vehicle control) in complete media for 24 hours and were then processed for analysis of receptor expression using flow cytometry. Phycoerythrin (PE)-labeled primary antibodies recognizing canine CD-14, TLR-2, and TLR-4 were used to evaluate receptor expression using direct immunofluorescence labeling and flow cytometry analysis. Briefly, triplicate cell aliquots in cold buffer (PBS containing 10% FBS and 1% sodium azide) were incubated with primary antibody (10-20 µl) for 45 minutes at room temperature under low light conditions. Cells were washed three times and resuspended in 100 µl of buffer for analysis using a FACS Array instrument. Unlabeled cells and cells labeled with antibody alone served as controls.

Phagocytosis: Canine primary monocytes were seeded ($1 \times 10^6$ cells/well) onto 6 well plates and allowed to recover for 24 hours. Cells were then treated with the indicated concentrations of OxBC or vehicle control (DMSO) for 24 hours. Cells treated with phorbol myristate acetate (PMA, 25 ng/mL) were used as positive controls and untreated cells were used as negative controls. Following treatment culture media was removed, cells were washed with buffer, and fresh culture media containing fluorescently labeled latex beads was added. For negative control cells the fresh media contained 5 µL of latex bead solution, for OxBC and vehicle control groups the fresh media contained the indicated concentration of OxBC or DMSO combined with 5 µL of latex bead solution, media for the positive control group contained PMA combined with 5 µL of latex bead solution. Cells were then allowed to phagocytos the latex beads during a 2-hour incubation. Following the incubation unengulfed beads were removed by multiple washings and cells were prepared for analysis by flow cytometry. OxBC's ability to enhance monocyte-phagocytic activity was evaluated by determining the amount of engulfed beads using fluorescent detection by FACS analysis.

QRT-PCR Evaluation of Inflammatory Regulators: Canine fibroblasts (CF52.Tr) were seeded ($1 \times 10^6$ cells/well) onto a 6 well plate and were pre-treated with OxBC (5 µM) or vehicle control (DMSO) for 24 hours. Following pre-treatment culture media was removed and replaced with fresh media. Under the naïve treatment model the fresh media contained OxBC (5 µM) or equivalent concentration of DMSO. Under the challenge treatment model fresh media contained OxBC (5 µM) or equivalent concentration of DMSO combined with LPS (30 µg). Cells were incubated for an additional 4 hours and were then processed for total RNA isolation. RNA (0.5 µg) was reverse transcribed to cDNA in a 20 µL reaction volume and 1 µL, of cDNA was used as template for quantitative real-time PCR (QRT-PCR) analysis of gene-expression using SYBR-green chemistry. Relative gene expression levels were calculated using β-actin as an internal control with correction for different PCR efficiencies. Treatment effects on gene-expression are shown relative to untreated control cells and OxBC's ability to reduce expression of pro-inflammatory chemokines was evaluated by comparison to cells treated with LPS alone.

Figure 5:
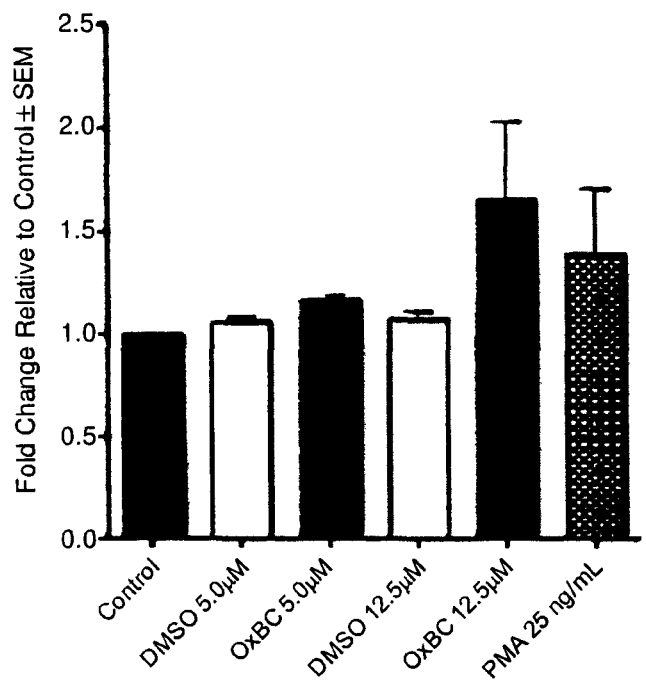
FIG. 5 is a graph showing the effect of OxBC on phagocytic activity of canine primary monocytes. Cells were incubated with the indicated concentrations of OxBC or vehicle control (DMSO) for 24 hours and then allowed to recover in the absence of compound for an additional 24 hours. Phagocytic activity was determined by measuring the cellular uptake of fluorescently labeled micro beads using a FACS array instrument. Treatment effects are expressed relative to untreated control cells. Phorbol myristate acetate (PMA) was used as a positive control. Results indicate that OxBC is able to enhance the phagocytic activity of canine monocytes leading to a faster and more efficient reactions to invading bacterial pathogens.

Results: Results shown in FIGS. 2-4 demonstrate the ability of OxBC to increase the abundance of pathogen sensing innate immune receptors in multiple canine cells types. OxBC treatment induced increases in surface expression of the toll-like receptor subtypes-2 and 4 as well as CD-14. These receptors are responsible for alerting the immune system to the presence of invading bacterial pathogens. OxBC's ability to up-regulate expression of these immune receptors in cell types such as osteoblasts and chondrocytes which are not primary effectors of the immune system but which play a secondary role in immunity highlights the potential for OxBC to significantly enhance immunity at the tissue level. At a functional level OxBC treatment of canine primary monocytes induced an increase in phagocytic activity (FIG. 5). Phagocytosis is a fundamental mechanism used by innate immune effectors to clear invading pathogens. Taken together these results suggest that OxBC acts to prime the canine innate immune system to more efficiently detect and respond to incipient bacterial infections.

Results shown in FIG. 6 demonstrate OxBC's ability to reduce the expression level of certain chemokine regulators of inflammation in the context of a pro-inflammatory challenge with bacterial lipopolysaccharide (LPS). MCP-1 and RANTES play an important role in directing the inflammatory response by serving as chemoattractants to recruit various immune cells including macrophages and lymphocytes to sites of injury or infection. Although an appropriate inflammatory response is a vital component of immune defense, disregulation of the inflammatory response, leading to over-activation, is associated with several chronic diseases such as rheumatoid arthritis. Several studies report that over-expression of chemokines such as MCP-1 and RANTES is associate with inflammatory joint diseases including arthritis. OxBC's ability to reduce the expression of these proinflammatory chemokines may represent an underlying mechanism to explain the improvement in mobility and activity levels observed for some of the dogs in the OxBC-clinical trial.

Other Embodiments

All publications and patent applications, and patents mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

We claim:

1. A method of reducing shedding in a canine animal in need thereof, said method comprising administering to said canine animal a composition comprising an oligomeric material in an amount sufficient to reduce shedding, wherein said oligomeric material is formed by reaction of 6 to 8 molar equivalents of oxygen with a carotenoid and has a median molecular weight of about 900 Daltons, and wherein from 0.1 mg/kg body weight to 3 mg/kg body weight of said oligomeric material is administered to said canine animal daily.

2. The method of claim 1, wherein said composition is mixed with food and administered orally to said canine animal.

3. The method of claim 2, wherein said food is a wet animal food or a dry animal food or said food is in the form of a kibble, a chew, a tablet, or a soft edible treat.

4. The method of claim 1, wherein said composition is administered to said canine animal as an oral supplement.

5. The method of claim 4, wherein said oral supplement is a palatable paste or gel.

6. The method of claim 5, wherein said paste or gel comprises from 2 mg/tablespoon to 750 mg/tablespoon of said oligomeric.

7. The method of claim 1, wherein said canine animal is a mature canine animal.

8. The method of claim 1, wherein said composition is provided in a comestible solid composition in a unit dosage form comprising from 2 mg to 130 mg of said oligomeric material and is formulated to be palatable to canines.

9. The method of claim 8, wherein said comestible solid composition in a unit dosage form is a kibble, a chew, a tablet, or a soft edible treat.

10. The method of claim 8, wherein said comestible solid composition in a unit dosage form is a chewable tablet and wherein said unit dosage form comprises from 2 mg to 75 mg of said oligomeric material.

11. A method of increasing joint mobility of a canine animal having poor joint mobility or increasing the activity level in a canine animal having a low activity level, said method comprising administering to said canine animal a composition comprising an oligomeric material in an amount sufficient to increase said joint mobility or increase said activity level, wherein said oligomeric material is formed by reaction of 6 to 8 molar equivalents of oxygen with a carotenoid and has a median molecular weight of about 900 Daltons, and wherein from 0.1 mg/kg body weight to 3 mg/kg body weight of said oligomeric material is administered to said canine animal daily.

12. The method of claim 11, wherein said composition is mixed with food and administered orally to said canine animal.

13. The method of claim 12, wherein said food is a wet animal food or a dry animal food or said food is in the form of a kibble, a chew, a tablet, or a soft edible treat.

14. The method of claim 11, wherein said composition is administered to said canine animal as an oral supplement.

15. The method of claim 14, wherein said oral supplement is a palatable paste or gel.

16. The method of claim 15, wherein said paste or gel comprises from 2 mg/tablespoon to 750 mg/tablespoon of said oligomeric material.

17. The method of claim 11, wherein said canine animal is a mature canine animal.

18. The method of claim 11, wherein said composition comprising is provided in a comestible solid composition in a unit dosage form comprising from 2 mg to 130 mg of said oligomeric material and is formulated to be palatable to canines.

19. The method of claim 18, wherein said comestible solid composition in a unit dosage form is a kibble, a chew, a tablet, or a soft edible treat.

20. The method of claim 18, wherein said comestible solid composition in a unit dosage form is a chewable tablet and wherein said unit dosage form comprises from 2 mg to 75 mg of said oligomeric material.

21. A method of reducing discoloration in an eye of a canine animal having pigmentation spots in said eye, said method comprising administering to said canine animal a composition comprising an oligomeric material in an amount sufficient to reduce said discoloration, wherein said oligomeric material is formed by reaction of 6 to 8 molar equivalents of oxygen with a carotenoid and has a median molecular weight of about 900 Daltons, and wherein said discoloration is discoloration arising from said pigmentation spots, and wherein from 0.1 mg/kg body weight to 3 mg/kg body weight of said oligomeric material is administered to said canine animal daily.

22. The method of claim 21, wherein said composition is mixed with food and administered orally to said canine animal.

23. The method of claim 22, wherein said food is a wet animal food or a dry animal food or said food is in the form of a kibble, a chew, a tablet, or a soft edible treat.

24. The method of claim 21, wherein said composition is administered to said canine animal as an oral supplement.

25. The method of claim 24, wherein said oral supplement is a palatable paste or gel.

26. The method of claim 25, wherein said paste or gel comprises from 2 mg/tablespoon to 750 mg/tablespoon of said oligomeric material.

27. The method of claim 21, wherein said canine animal is a mature canine animal.

28. The method of claim 21, wherein said composition is provided in a comestible solid composition in a unit dosage form comprising from 2 mg to 130 mg of said oligomeric material and is formulated to be palatable to canines.

29. The method of claim 28, wherein said comestible solid composition in a unit dosage form is a kibble, a chew, a tablet, or a soft edible treat.

30. The method of claim 28, wherein said comestible solid composition in a unit dosage form is a chewable tablet and wherein said unit dosage form comprises from 2 mg to 75 mg of said oligomeric material.

* * * * *